US006412352B1

United States Patent
Evans et al.

(10) Patent No.: US 6,412,352 B1
(45) Date of Patent: Jul. 2, 2002

(54) METHOD AND APPARATUS FOR MEASURING THE MASS FLOW RATE OF A FLUID

(75) Inventors: Robert P. Evans; S. Curtis Wilkins, both of Idaho Falls; Lorenzo D. Goodrich, Shelley; Jonathan D. Blotter, Pocatello, all of ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/533,523

(22) Filed: Mar. 23, 2000

Related U.S. Application Data

(60) Provisional application No. 60/125,899, filed on Mar. 24, 1999.

(51) Int. Cl.[7] .............................. G01F 1/74; G01N 29/00
(52) U.S. Cl. ....................................... 73/861.04; 73/592
(58) Field of Search ............................. 73/861.04, 592, 73/587, 861.18, 40.5 A, 19.03; 702/50, 45, 57, 100

(56) References Cited

U.S. PATENT DOCUMENTS

| | | | |
|---|---|---|---|
| 4,007,754 A | * | 2/1977 | Beck et al. ..................... 137/2 |
| 4,787,252 A | * | 11/1988 | Jacobson et al. ........ 73/861.28 |
| 5,051,922 A | * | 9/1991 | Toral et al. .............. 73/861.04 |
| 5,121,639 A | * | 6/1992 | McShane ................. 73/861.04 |
| 5,148,405 A | | 9/1992 | Belchamber et al. ......... 367/13 |
| 5,207,107 A | | 5/1993 | Wolf et al. .............. 73/861.04 |
| 5,218,871 A | | 6/1993 | Cody et al. .............. 73/861.04 |
| 5,343,040 A | | 8/1994 | Girgis ........................ 364/484 |
| 5,415,048 A | | 5/1995 | Diatschenko et al. .... 73/861.04 |
| 5,741,980 A | | 4/1998 | Hill et al. ................. 73/861.04 |
| 5,756,898 A | | 5/1998 | Diatschenko et al. ......... 73/592 |
| 5,770,805 A | | 6/1998 | Castel ...................... 73/861.04 |
| 5,907,104 A | * | 5/1999 | Cage et al. ............ 73/861.355 |

OTHER PUBLICATIONS

Evans, Robert P., "Two–Phase Mass Flow Measurement Using Noise Analysis," 45th International Instrumentation Symposium, ISA—International Society for Measurement and Controls, May 2–6, 1999.
Evans, Robert P., "Geothermal Mass Flow Measurement Feasiblity Report," Department of Energy Geothermal Conference, May 18–20, 1999.

* cited by examiner

*Primary Examiner*—Harshad Patel
(74) *Attorney, Agent, or Firm*—Workman Nydegger & Seeley

(57) ABSTRACT

A non invasive method and apparatus is provided to measure the mass flow rate of a multi-phase fluid. An accelerometer is attached to a pipe carrying a multi-phase fluid. Flow related measurements in pipes are sensitive to random velocity fluctuations whose magnitude is proportional to the mean mass flow rate. An analysis of the signal produced by the accelerometer shows a relationship between the mass flow of a fluid and the noise component of the signal of an accelerometer. The noise signal, as defined by the standard deviation of the accelerometer signal allows the method and apparatus of the present invention to non-intrusively measure the mass flow rate of a multi-phase fluid.

25 Claims, 6 Drawing Sheets

METHOD AND APPARATUS FOR MEASURING THE MASS FLOW RATE OF A FLUID

RELATED APPLICATION

This application claims priority from United States provisional application S/No. 60/125,899 filed Mar. 24, 1999.

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

BACKGROUND OF THE INVENTION

1. Field of the Invention

The present invention relates to a method for measuring the mass flow rate of a multiple component, multi- phase fluid. More particularly, the present invention relates to a method for measuring the mass flow rate of a two phase fluid

2. Present State of the Art

In many applications, including geothermal applications, fluids are transported from one place to another. Often, the fluid is a multi-phase fluid meaning that it exists in one or more states. With regard to geothermal applications, the fluid is typically water and is in both a liquid and gaseous state. Because the fluid is being transported while in a multi-phase form, it is desirous to measure fluid flow related rates. The measurement of the mass flow rate is particularly useful.

Measuring the mass flow rate, however, has proven problematic. Early attempts to measure mass flow rate involved the use of intrusive or invasive devices, which involve placing some sort of sensor within the pipe that is transporting the multi-phase fluid. Intrusive mass flow measurement devices have not proven satisfactory. In many cases, including geothermal and petroleum applications, the fluid contains a wide variety of minerals and other compounds that are deposited on the measuring device, rendering the measuring device inaccurate or inoperable.

Another method of measuring mass flow rate involves the use of pressure ports. This method is less invasive than the method described above, but is subject to the same considerations. The chemical composition of the fluid may ultimately corrode or plug the pressure port, resulting in an inability to continuously provide mass flow rates.

Some external methods exist for measuring flow rates, but these methods require multiple sensors, compilations of data representing known fluid flows and complex mathematical manipulations. Preferably, a flow meter can determine the composition of flowing fluids without impeding the flow or reacting with the fluids. Clearly, invasive measurement devices do not satisfy this requirement. An external device and method capable of measuring the mass flow rate of a fluid without interfering with the fluid flow or reacting with the fluid is desirable.

OBJECTS AND SUMMARY OF THE INVENTION

The present invention has been developed in response to the present state of the art, and in particular, in response to these and other problems and needs that have not been fully or completely solved by currently available methods and apparatus for measuring fluid mass flow rates. Thus, it is an overall object of the present invention to provide a method and apparatus for reliably and non invasively measuring the mass flow rates of multi-phase fluids.

It is another object of one embodiment of the present invention to measure the mass flow rate of a multi-phase fluid without interfering with the fluid flow.

It is a further object of one embodiment of the present invention to measure the mass flow rate of a multi-component, multi-phase fluid.

In summary, the foregoing and other objects are achieved by providing a method and apparatus for measuring the mass flow rate of a multi-phase fluid. One embodiment of the present invention uses an accelerometer attached to a pipe which is transporting a multi-phase fluid. The multi-phase fluid flow is turbulent and produces vibrations in the pipe, which are measured by the accelerometer. In addition to the primary signal of the accelerometer, various noise components are superimposed on the primary signal. By analyzing the noise component, as defined by the standard deviation of the accelerometer signal, the mass flow rate of the fluid can be determined.

The analysis of the data produced by the accelerometer shows a definite relationship between the mass flow rate of the fluid and the noise component of the signal produced by an externally mounted accelerometer. In addition to measuring the mass flow rate of a multi-phase fluid, the present invention is non invasive.

Additional objects and advantages of the present invention will be set forth in the description which follows, and in part will be obvious from the description, or may be learned by the practice of the invention. The objects and advantages of the invention may be realized and obtained by means of the instruments and combinations particularly pointed out in the appended claims. These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

The present invention provides methods and apparatus for measuring the mass flow of a fluid. As used herein, fluid includes solids, liquids and gases, but is usually associated with liquid and gas fluid phases. Multi-phase fluid includes a fluid having, for example, a liquid portion and a gaseous portion. Multi-component fluid indicates that the fluid comprises different compounds or substances. For example, a geothermal fluid may contain water and minerals.

Figure 1:
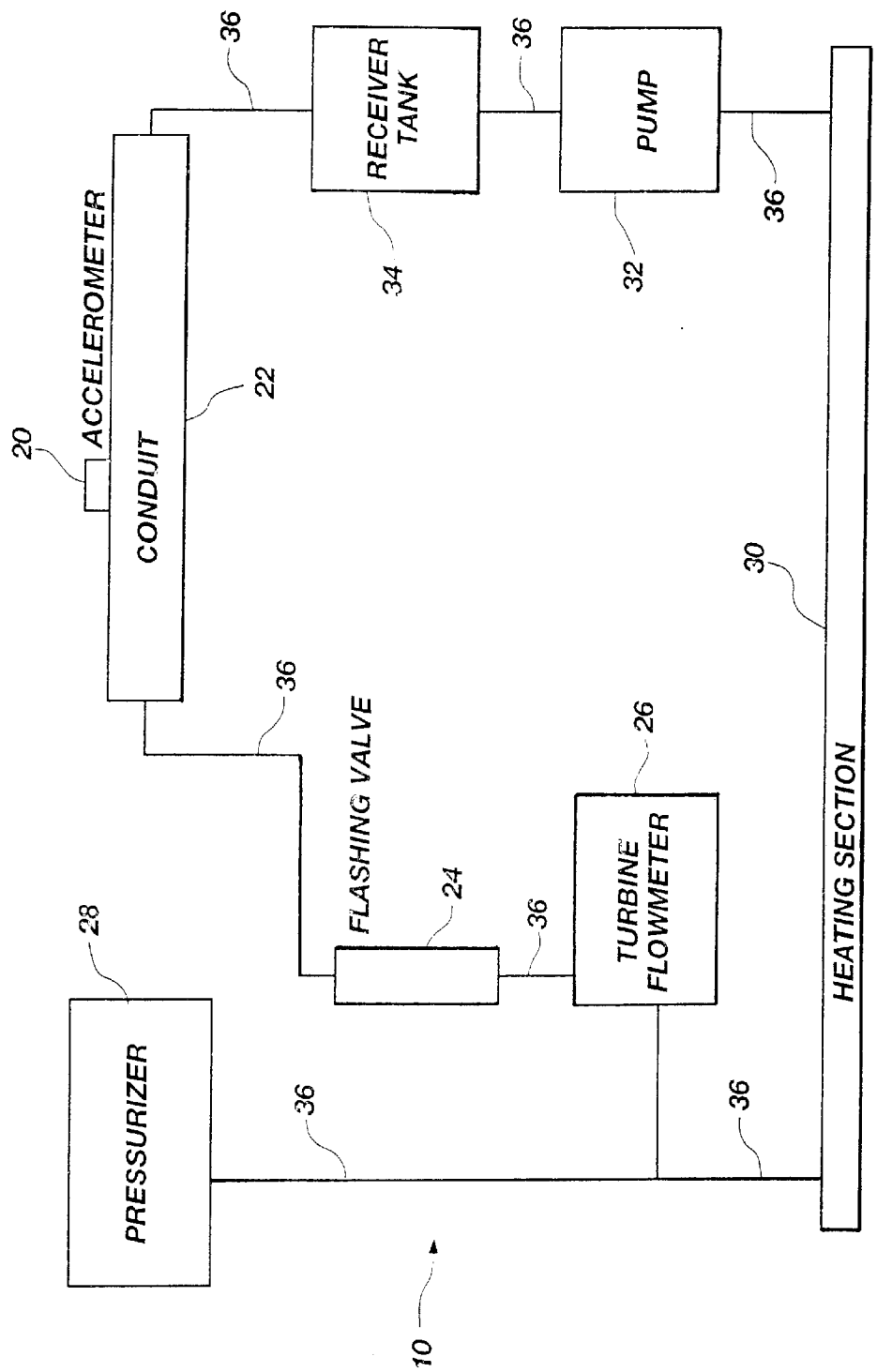
FIG. 1 is a block diagram of a system used to evaluate one embodiment of the present invention.

FIG. 1 is an block diagram of one embodiment of a flow loop for testing the present invention. Illustrated in FIG. 1 is a flow loop 10 used to create a multi-phase fluid flow. In this example, flow loop 10 is circulating water with a constant speed pump 32. The water is heated in heating section 30 and system pressure is maintained in flow loop 10 by pressurizer 28. After the water is heated, the water passes through turbine flowmeter 26. Turbine flowmeter 26 also measures the mass flow of the water and is used as a reference measurement for flow loop 10. The method and apparatus of the present invention does not require turbine flowmeter 26 in non-test situations.

After passing through turbine flowmeter 26, the water enters flashing valve 24. Flashing valve 24 creates a multi-phase fluid flow which then enters conduit 22. Conduit 22 is the portion of flow loop 10 where the mass flow of the multi-phase water is measured. Conduit 22 provides a path for the fluid flow and is typically embodied as a pipe. Accelerometer 20 is mounted to conduit 22 and senses the vibrations of conduit 22. After the multi-phase fluid flow passes through conduit 22, the fluid goes to receiver tank 34. The water is then recirculated through flow loop 10 by pump 32. Flow loop 10 in FIG. 1 may comprise additional flow loop elements, but the purpose of flow loop 10 is to create a multi-phase fluid flow such that the mass flow rate of the multi-phase fluid may be measured. Note that accelerometer 20 is mounted to the exterior of conduit 22 and is therefore capable of measuring the mass flow rate of a fluid in a non-invasive manner.

In FIG. 1, the mass flow rate of the multi-phase fluid is measured in conduit 22, which is representative of situations where a mass flow measurement is desired. For example, the pipes used to transport geothermal fluid or petroleum are embodiments of conduit 22. The mass flow rate of the multi-phase fluid in conduit 22 is difficult to measure because the fluid comprises more than one phase and the fluid flow is turbulent.

Figure 3:
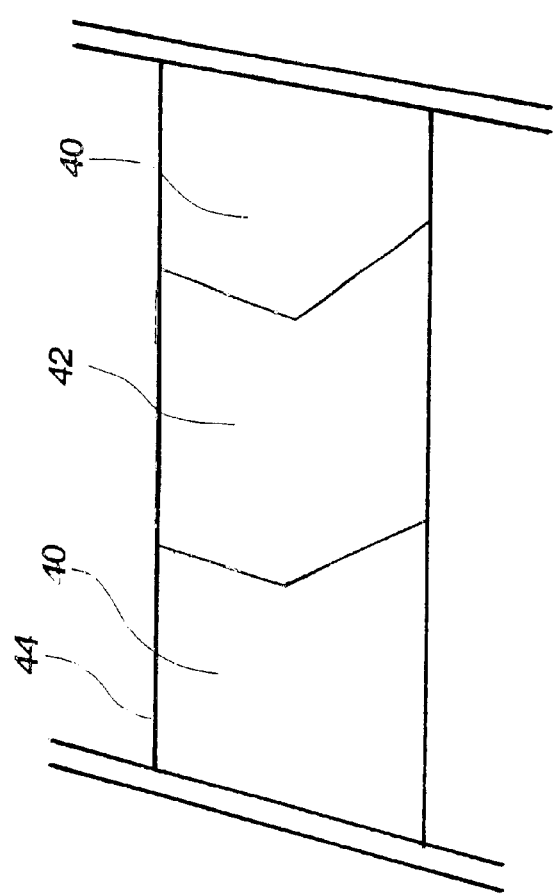
FIG. 3 is a lengthwise cross section of a pipe carrying a fluid exhibiting slug flow.
Figure 2:
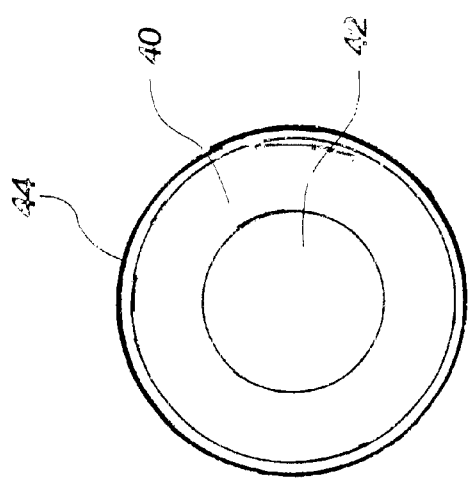
FIG. 2 is a cross section of a pipe carrying a fluid exhibiting annular flow.

One example of how a fluid may flow is illustrated in FIG. 2. FIG. 2 is a cross section of a pipe carrying a multi-phase fluid exhibiting the characteristics of annular flow. In FIG. 2, pipe 44 contains liquid fluid 40 around gaseous fluid 42. In an annular flow the liquid portion of the fluid flow forms a ring around the gaseous portion of the fluid flow. Another example of how a fluid may flow is illustrated in FIG. 3, which shows a fluid exhibiting slug flow. In slug flow, pipe 44 contains a section of liquid fluid 40 followed by a section of gaseous fluid 42, followed by another section of liquid fluid 40. This pattern is repeated for the fluid flow.

These and other types of fluid flow make it difficult to determine the total mass flow of the fluid because the percentage of liquid fluid and gaseous fluid is unknown. The ratio of the mass of gaseous fluid to the mass of the liquid fluid is referred to as the quality of the fluid flow.

Figure 4:
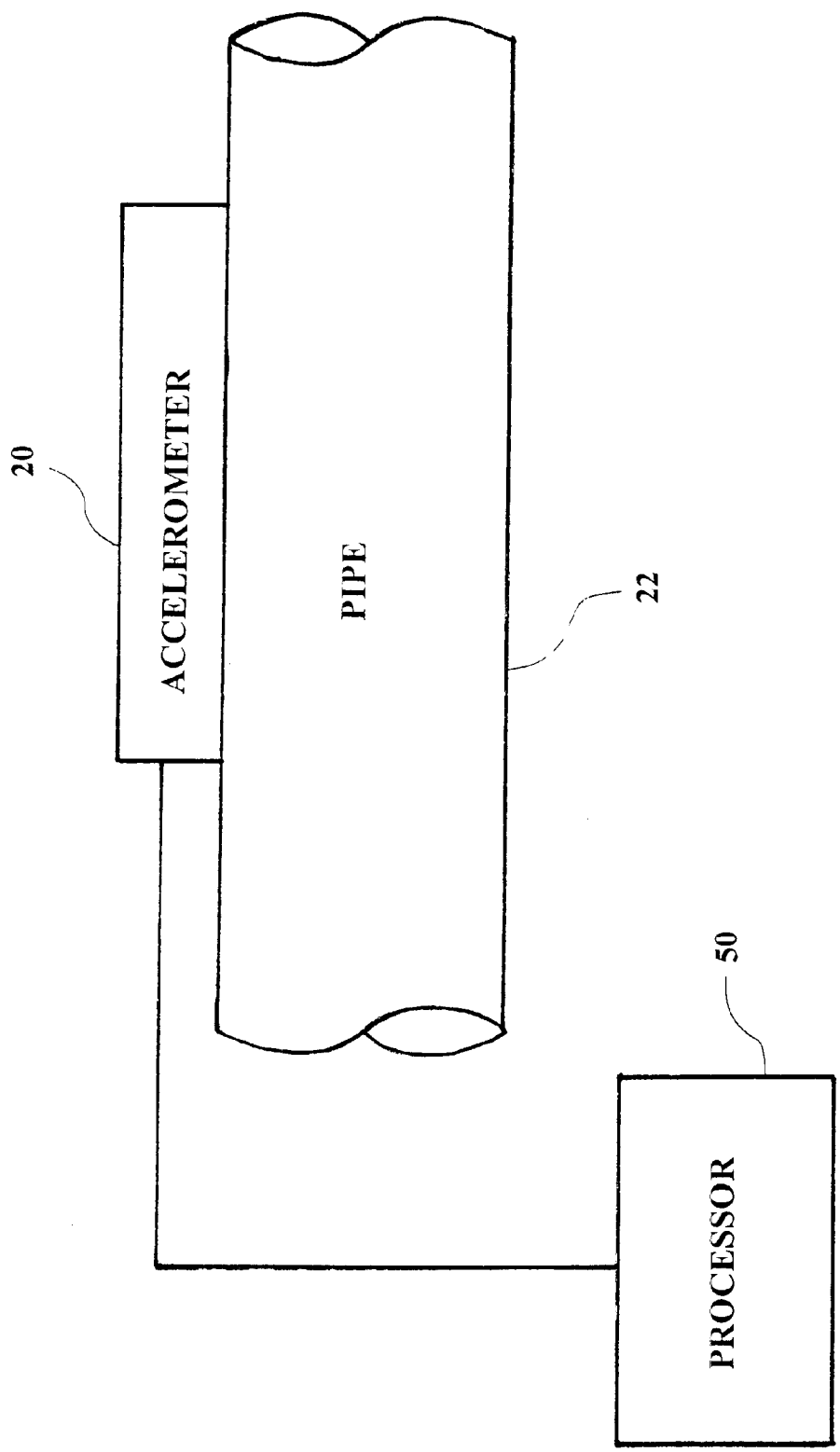
FIG. 4 is a block diagram of one embodiment of a system for measuring the mass flow rate of a multi-phase fluid.

The fluid flow parameters of a multi-phase fluid in a pipe or conduit can be measured however. Fluid flow parameters include but are not limited to fluid velocity and mass flow rate. FIG. 4 is a block diagram of one embodiment of a system for measuring the mass flow rate of a multi-phase fluid. In FIG. 4, accelerometer 20 is mounted to conduit 22. Preferably, accelerometer 20 is mounted perpendicularly to the outer surface of conduit 22. The multi-phase fluid flow in conduit 22 is turbulent and causes conduit 22 to vibrate or react to the turbulent fluid flow. These vibrations are measured by accelerometer 20 and accelerometer 20 produces a signal representative of the vibrations present in conduit 22. An accelerometer is an example of sensor means for sensing fluid flow characteristics. Fluid flow characteristics include characteristics of the fluid such as velocity and pressure as well as indications of fluid flow such as vibrations in the conduit and pressure differences. It will be appreciated by one of skill in the art that measured values of such fluid flow characteristics may be used to derive values of related fluid flow characteristics, in accordance with various flow calculation methods and formulae well known in the art.

The signal produced by accelerometer 20 is transmitted to processor 50. Processor 50 analyzes the signal and ultimately produces the mass flow rate of the fluid. The signal produced by accelerometer 20 can be divided into several components. In flow loop 10, shown in FIG. 1, some of the components of the signal produced by accelerometer 20 were attributable to pump 32 and other elements of flow loop 10. With regard to the fluid flow, flow related measurements in pipes are sensitive to random velocity fluctuations whose magnitude is proportional to the mean velocity flow. The primary signal produced by any sensor or transducer sensing a condition related to fluid flow will have, in addition to its usual signal, various noise components superimposed upon the primary signal. The various noise components are produced by the random velocity fluctuations of the fluid flow. The noise components of the accelerometer signal may be represented by the standard deviation of the mean flow velocity. In other words, the noise components are represented by the standard deviation from the mean accelerometer signal. Processor 50 is an example of processor means for analyzing the accelerometer signal and for determining the mass flow rate of the fluid.

In one embodiment, accelerometer 20 is sampled at a user defined frequency. For example, accelerometer could be sampled 1000 times per second. These samples are averaged by processor 50 to produce a mean accelerometer signal. The standard deviation of the mean accelerometer signal is computed by processor 50 and is representative of the noise component of the signal. This noise signal is correlated to the mass flow rate of the fluid. It will be appreciated by one of skill in the art that the calculation of basic statistical parameters such as the mean and standard deviation of a body of data compiled, for example, by sampling of sensors such as accelerometer 20, may be readily accomplished by way of various well known statistical methods and formulae.

Figure 5:
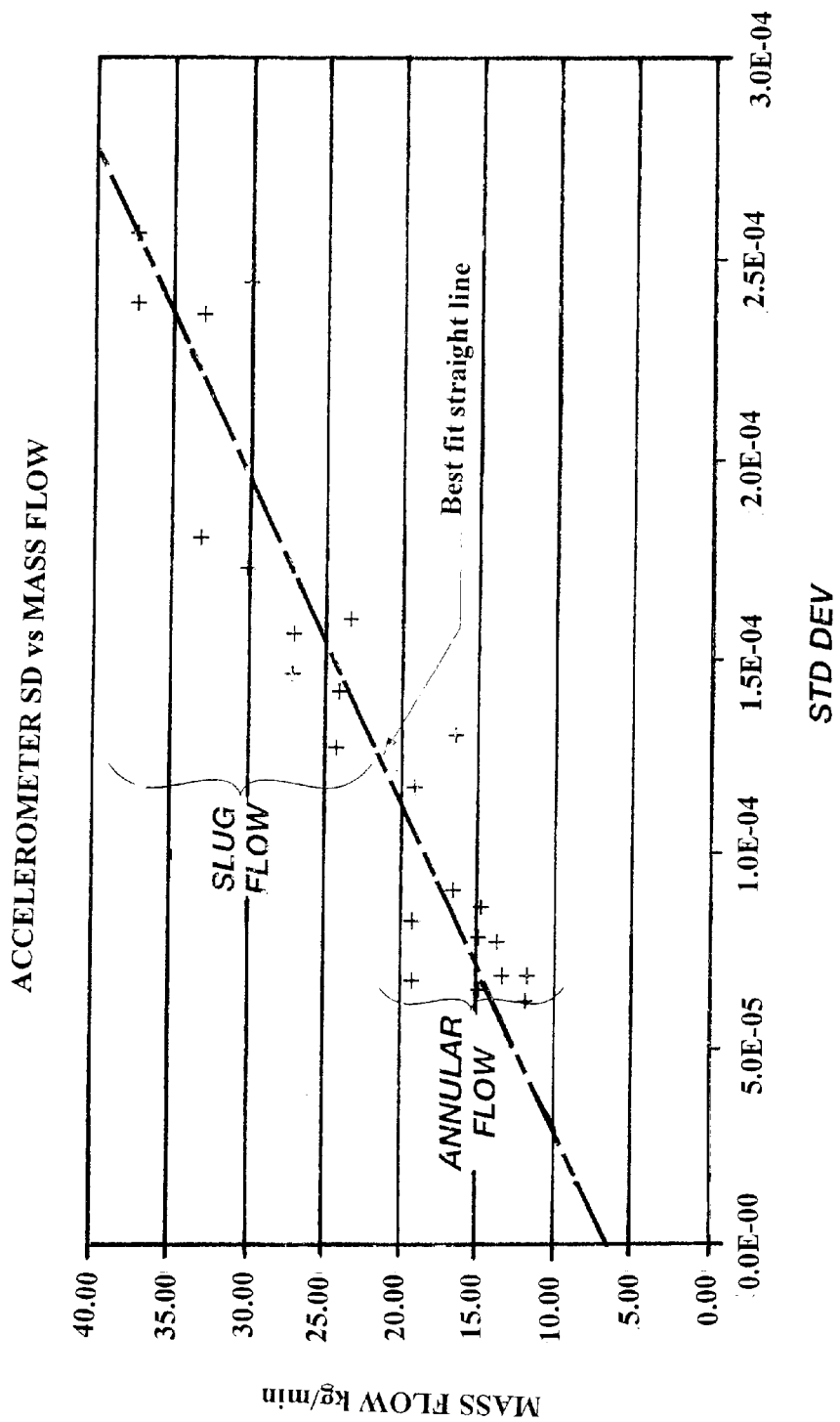
FIG. 5 is a graph representing the standard deviation of an accelerometer plotted against the mass flow of a fluid flow.

For the fluid flow in FIGS. 1 and 5, accelerometer data were recorded for a wide variety of fluid flows including single phase, two phase, annular flow and slug flow. The accelerometer data were analyzed with processor 50 by performing a power spectral density analysis, which showed that the accelerometer data contained a very large 60 Hz component and associated harmonics. As described above, these components are related to the pump and other flow loop elements and were notch filtered. The power density analysis and the notch filtering are not necessary to the method of the present invention, but simplify the analysis.

Figure 6:
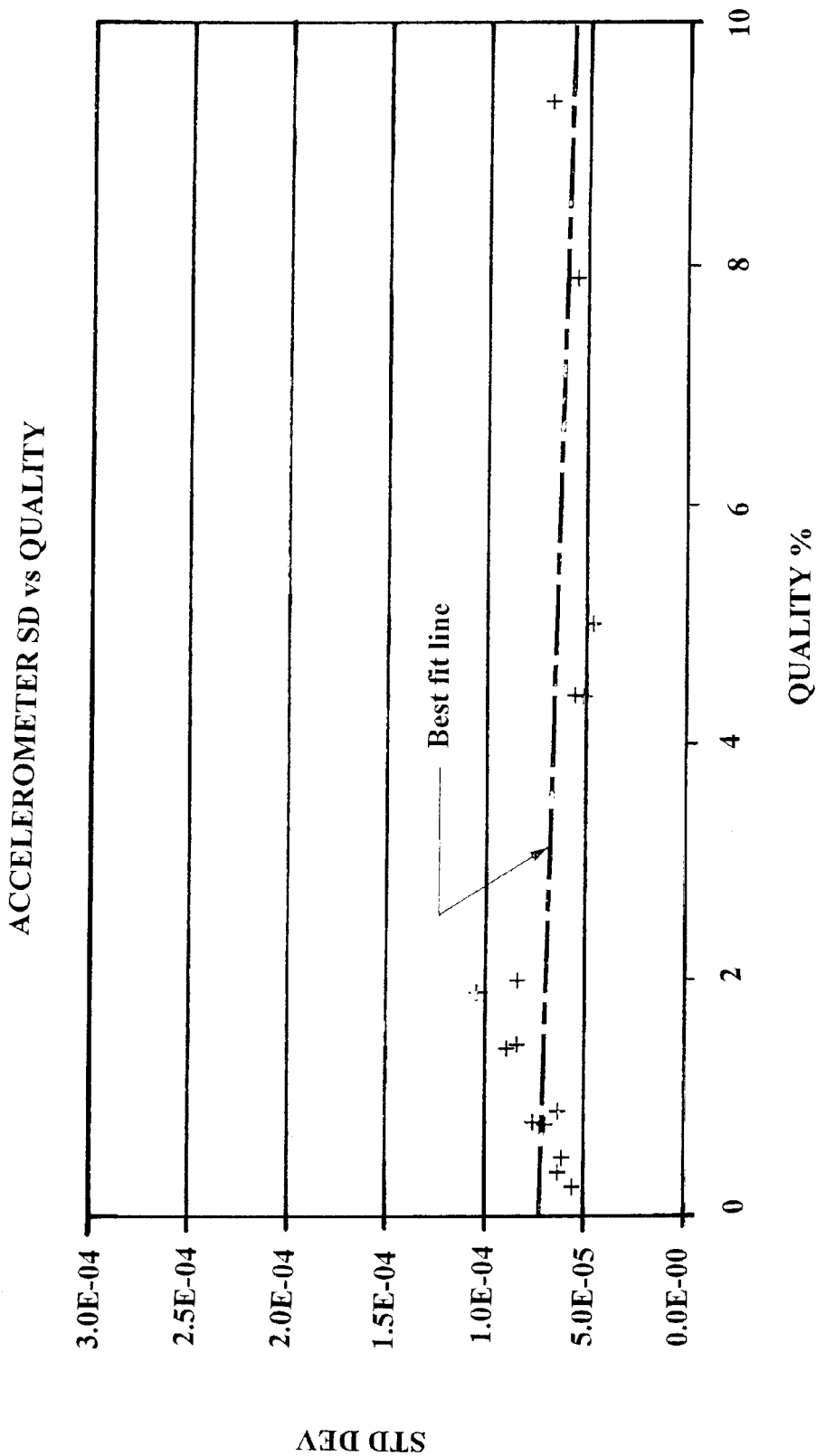
FIG. 6 is a graph representing the quality of the fluid plotted against the standard deviation of an accelerometer.

The remaining components of the accelerometer signal were then divided into two groups. The first group comprised data where the mass flow was constant and the quality of the fluid changed. The second group of data comprised data where the mass flow varied and the quality was held constant. FIG. 5 illustrates the mass flow plotted against the standard deviation of the accelerometer signal for the second group of data. FIG. 6 illustrates the standard deviation of the accelerometer signal plotted against the quality of the fluid flow for the first group of data. FIGS. 5 and 6 indicate a relationship between the standard deviation of the accelerometer signal and the mass flow rate of the fluid. The standard deviation is then correlated to the mass flow rate of the fluid.

Figure 7:
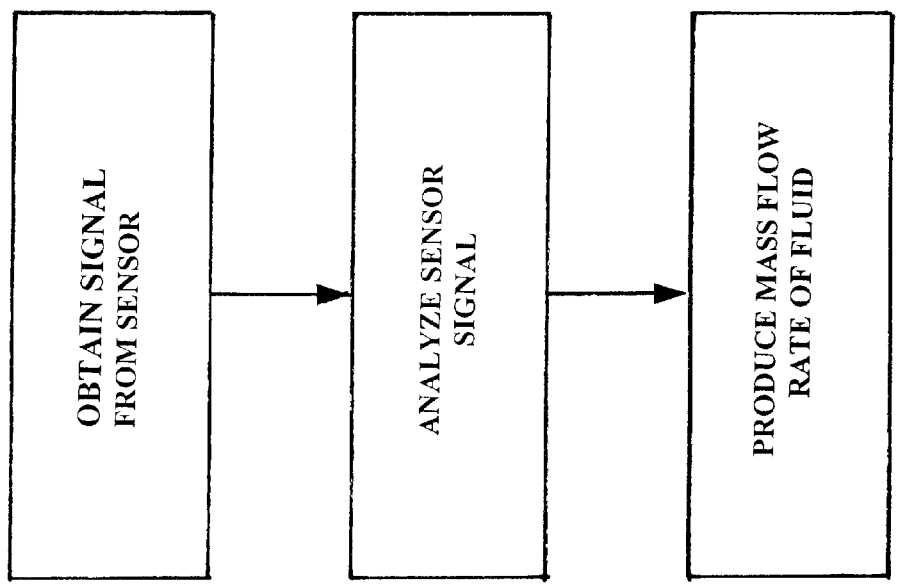
FIG. 7 is a flow chart of one embodiment of a method for measuring the mass flow rate of a multi-phase fluid.

FIG. 7 is a flow chart of the method for measuring the mass flow rate of a multi-phase fluid flow. In step 60, a signal is obtained from a sensor. The sensor is typically mounted to the exterior of a pipe and is capable of sensing characteristics of the fluid flow within the pipe. The sensors used to accomplish this task include accelerometers, differential pressure sensors, temperature sensors and others. The signal obtained from the sensor has several components, one of which is a noise component which is related to the random velocity fluctuations of the multi-phase fluid flow. If a differential pressure sensor is used, the noise component is related to random pressure fluctuations of the multi-phase fluid flow.

In step 62, the signal produced by the sensor is analyzed. The analysis of the signal can include a power density spectrum analysis that enables the components of the signal not related to the fluid flow to be filtered out. As described above, the power density spectrum analysis is not necessary, but simplifies the analysis of the accelerometer signal. The analysis of the signal includes calculating the mean of the signal and determining the standard deviation of that signal. The noise component of the signal, as defined by the standard deviation, is representative of the mass flow rate.

In step 64, the standard deviation of the fluid flow is correlated to a mass flow rate. In other words, the relationship between the standard deviation and the mass flow rate of the fluid permit the calculation of the mass flow rate upon determining the standard deviation. In one embodiment, the correlation of the standard deviation to the mass flow rate is done by calibrating the accelerometer. The purpose of turbine flowmeter 26 in FIG. 1 is to provide a reference for accelerometer 20 such that accelerometer 20 can be calibrated. It will be appreciated that such calibration processes are well known in the art. Once accelerometer 20 is calibrated, it can be used without the presence of turbine flowmeter 26 to determine the mass flow rate of a fluid.

The present invention has been described in terms of using an accelerometer, but can be applied to intrusive measurements such as pressure, differential pressure, temperature and momentum flux measurements. Further, the present invention has been described principally in terms of a water flow comprising liquid water and steam. The present invention extends to other fluids and includes multi-phase fluids as well as multi-component fluids. An important aspect of the present invention is that the method is not invasive or intrusive and is not therefore subject to the corrosive effects of the fluid.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A method of measuring a mass flow rate of a multi-phase fluid flow within a conduit comprising the steps of:
   producing a signal from the fluid flow in the conduit;
   separating a noise component from a primary component of the signal;
   determining a standard deviation of the noise component; and
   correlating the standard deviation to a mass flow rate of the multi-phase fluid flow.

2. The method of claim 1 further comprising the step of performing a power spectral density analysis to remove a component of the signal not related to the multi-phase fluid flow.

3. The method of claim 1 wherein the step of producing a signal from the fluid flow further comprises the step of non-invasively attaching sensor means for sensing fluid flow characteristics to the conduit.

4. The method of claim 1, wherein the signal is produced with an accelerometer.

5. The method of claim 1, wherein the signal is produced with a differential pressure sensor.

6. The method of claim 1, wherein the signal is produced with a momentum flux sensor.

7. The method of claim 1 further comprising the step of calibrating the signal produced from the fluid flow.

8. A non-intrusive method of measuring a mass flow rate of a multi-phase fluid within a conduit comprising:
   receiving a signal produced by sensor means for sensing fluid flow characteristics attached to the conduit;
   seperating a noise component from the signal;
   analyzing the signal to produce a standard deviation of the signal produced by the sensor means; and
   deriving the mass flow rate of the multi-phase fluid from the standard deviation of the signal.

9. The method of claim 8, wherein the noise component is defined by the standard deviation of the signal.

10. A method of measuring fluid flow parameters of a fluid in a conduit comprising the steps of:
    placing sensor means for sensing fluid flow characteristics in contact with the fluid conduit to sense at least one fluid flow characteristic of the fluid flow passing through the conduit;
    placing sensor means for sensing fluid flow characteristics in contact with the fluid conduit to sense fluid flow characteristics of the fluid flow passing through the conduit;
    analyzing a signal produced by the sensor means;
    separating a noise component from the signal;
    processing the noise component to obtain a standard deviation of the noise component; and
    correlating the standard deviation to a fluid flow parameter.

11. The method of claim 10, wherein the fluid flow parameter is the mass flow rate of the fluid.

12. The method of claim 10, wherein the sensor means for sensing fluid flow characteristics comprises an accelerometer.

13. The method of claim 10, wherein the sensor means for sensing fluid flow characteristics comprises a differential pressure sensor.

14. The method of claim 10 further comprising the step of calibrating the sensor means for sensing fluid flow characteristics.

15. An apparatus for measuring the mass flow rate of a multi-phase fluid in a conduit comprising:
- sensor means for sensing fluid flow characteristics configured for attachment to the conduit and producing a signal representative of the fluid flow, wherein the signal has a noise component superimposed on a primary component;
- processor means for analyzing the signal produced by the sensor means for sensing fluid flow characteristics, wherein the processor means calculates a standard deviation of the noise component and correlates the standard deviation to a mass flow rate of the multi-phase fluid.

16. The apparatus of claim 15, wherein the sensor means for sensing fluid flow characteristics comprises an accelerometer.

17. The apparatus of claim 15, wherein the sensor means for sensing fluid flow characteristics comprises a differential pressure sensor.

18. The apparatus of claim 15, wherein the noise component is related to random velocity fluctuations of the multi-phase fluid.

19. The apparatus of claim 15, wherein the noise component is related to random pressure fluctuations of the multi-phase fluid.

20. An apparatus suitable for measuring the mass flow rate of a fluid through a conduit, the fluid having at least one component and at least one phase, the apparatus comprising:
- sensor means for sensing fluid flow characteristics configured for attachment to the conduit and producing a signal corresponding to a characteristic of the fluid flow; and
- processor means for analyzing the signal produced by the sensor means for sensing fluid flow characteristics, wherein the processor means calculates a mean signal value and a standard deviation of the mean signal value representing a noise component of the signal.

21. The apparatus as recited in claim 20, wherein the noise component of the signal is related to random velocity fluctuations of the fluid.

22. The apparatus as recited in claim 20, wherein the noise component of the signal is related to random pressure fluctuations in the fluid.

23. The apparatus as recited in claim 20, wherein the mean signal value represents the mean velocity of the fluid.

24. The apparatus as recited in claim 20, wherein the sensor means for sensing fluid flow characteristics comprises an accelerometer.

25. The apparatus as recited in claim 20, wherein the characteristic of the fluid flow comprises random velocity fluctuations of the fluid.

* * * * *